United States Patent

Beams et al.

Patent Number: 5,863,931
Date of Patent: Jan. 26, 1999

[54] AMIDINO DERIVATIVES AND THEIR USE AS NITRIC OXIDE SYNTHASE INHIBITORS

[75] Inventors: Richard Mansfield Beams; Harold Francis Hodson; Richard Michael John Palmer, all of Beckenham, Great Britain

[73] Assignee: Glaxo Wellcome Inc., Research Triangle Park, N.C.

[21] Appl. No.: 256,032

[22] PCT Filed: Dec. 23, 1992

[86] PCT No.: PCT/GB92/02387

§ 371 Date: Jun. 22, 1994

§ 102(e) Date: Jun. 22, 1994

[87] PCT Pub. No.: WO93/13055

PCT Pub. Date: Jul. 8, 1993

[30] Foreign Application Priority Data

Dec. 24, 1991 [GB] United Kingdom .................. 9127376

[51] Int. Cl.[6] .................................................. A61K 31/44
[52] U.S. Cl. ..................... 514/357; 514/529; 514/531; 514/534; 514/549; 514/550; 514/551; 514/562; 514/563; 514/564; 546/332; 560/35; 560/124; 560/123; 560/150; 560/153; 560/168; 562/440; 562/505; 562/506; 562/556; 562/562; 562/560; 562/557
[58] Field of Search ..................... 562/440, 507, 562/505, 506, 556, 557, 560; 560/35, 125, 123, 124, 150, 153, 168; 514/529, 531, 534, 538, 549, 550, 551, 562, 563, 564, 331, 357, 365, 374, 428, 471; 546/246, 332; 548/199, 236, 561, 567; 549/494

[56] References Cited

FOREIGN PATENT DOCUMENTS

A-0097031 12/1983 European Pat. Off. .

Primary Examiner—Michael L. Shippen
Attorney, Agent, or Firm—Nixon & Vanderhye

[57] ABSTRACT

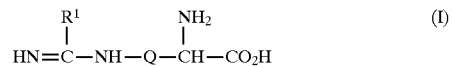

Amidino derivatives of formula (I) and salts, and pharmaceutically acceptable esters and amides thereof, in which: $R^1$ is a $C_{1-6}$ straight or branched chain alkyl group, a $C_{2-6}$alkenyl group, a $C_{2-6}$alkynyl group, a $C_{3-6}$cycloalkyl group or a $C_{3-6}$cycloalkyl$C_{1-6}$alkyl group; Q is an alkylene, alkenylene or alkynylene group having 3 to 6 carbon atoms and which may optionally be substituted by one or more $C_{1-3}$alkyl groups; a group of formula —$(CH_2)_pX(CH_2)_q$— where p is 2 or 3, q is 1 or 2 and X is $S(O)_x$ where x is 0, 1 or 2, O or $NR^2$ where $R^2$ is H or $C_{1-6}$alkyl; or a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$alkyl, $C_{1-6}$alkoxy, hydroxy, halo, nitro, cyano, trifluoro $C_{1-6}$alkyl, amino, $C_{1-6}$alkylamino or di$C_{1-6}$alkylamino; and pharmaceutical formulations containing them are described for use in medicine novel compounds of formula (I) and the preparation of such novel compounds are also disclosed.

6 Claims, No Drawings

AMIDINO DERIVATIVES AND THEIR USE AS NITRIC OXIDE SYNTHASE INHIBITORS

The present invention relates to amidino derivatives, to methods for their manufacture, to pharmaceutical compositions containing them and to their use in therapy, in particular their use as nitric oxide synthase inhibitors.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesised from the amino-acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991)). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least two types of NO synthase as follows:

(i) a constitutive, $Ca^{++}$/calmodulin dependent enzyme that releases NO for response to receptor or physical stimulation.

(ii) a $Ca^{++}$ independent enzyme which is induced after activation of vascular smooth muscle, macrophages, endothelial cells, and a number of other cells by endotoxin and cytokines. Once expressed this inducible NO synthase synthesises NO for long periods.

The NO released by the constitutive enzyme acts as a transduction mechanism underlying several physiological responses. The NO produced by the inducible enzyme is as a cytotoxic molecule for tumour cells and invading microorganisms. It also appears that the adverse effects of excess NO production, in particular pathological vasodilation and tissue damage, may result largely from the effects of NO synthesised by the inducible NO synthase.

The NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypotension and possible thrombosis and tissue damage. In particular, in the case of the therapeutic use of L-NMMA for the treatment of toxic shock it has been recommended that the patient must be subject to continuous blood pressure monitoring throughout the treatment. Thus, whilst non-selective NO synthase inhibitors have therapeutic utility provided that appropriate precautions are taken, NO synthase inhibitors which are selective in the sense that they inhibit the inducible NO synthase to a considerably greater extent than the constitutive NO synthase would be of even greater therapeutic benefit and much easier to use.

The present invention concerns amidino derivatives of the formula (I)

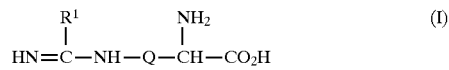

and salts, and pharmaceutically acceptable esters and amides thereof, in which:

$R^1$ is a $C_{1-6}$ straight or branched chain alkyl group, a $C_{2-6}$alkenyl group, a $C_{2-6}$alkynyl group, a $C_{3-6}$cycloalkyl group or a $C_{3-6}$cycloalkyl$C_{1-6}$alkyl group;

Q is an alkylene, alkenylene or alkynylene group having 3 to 6 carbon atoms and which may optionally be substituted by one or more $C_{1-3}$alkyl groups;

a group of formula —$(CH_2)_pX(CH_2)_q$— where p is 2 or 3, q is 1 or 2 and X is $S(O)_x$ where x is 0, 1 or 2, O or $NR^2$ where $R^2$ is H or $C_{1-6}$alkyl; or a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$alkyl, $C_{1-6}$alkoxy, hydroxy, halo, nitro, cyano, trifluoro$C_{1-6}$alkyl, amino, $C_{1-6}$alkylamino or di$C_1$-alkylamino.

The compounds of formula (I) may include a number of asymmetric centres in the molecule depending on the precise meaning of the various groups and formula (I) is intended to include all possible isomers. When the group Q is an alkenyl group such as —$CH_2CH=CHCH_2$—, both the E and Z isomers are included. The compounds of formula (I) all include an asymmetric centre in the group

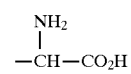

and although the natural L or (S) chirality of arginine is preferred, it is again intended that the formula should include all possible isomers.

The group A as a carbocyclic or heterocyclic ring may be saturated, may include ethylenic unsaturation or may be aromatic. In the case of a heterocyclic ring the ring may contain one or more heteroatoms which will generally be selected from N, O and S.

Pharmaceutically acceptable esters and amides of the compounds of formula (I) may have the —$CO_2H$ end group replaced by —$CO_2R^3$ where $R^3$ is for example $C_{1-6}$alkyl, aryl or aryl$C_{1-3}$alkyl or —$COR^4$ where $R^4$ is the residue of a suitable natural of synthetic amino acid.

According to one aspect, the present invention provides the use of a compound of formula (I) as defined above or a pharmaceutically acceptable salt, ester or amide thereof for use in the manufacture of a medicament for the treatment of a condition where there is an advantage in inhibiting NO production from L-arginine by the action of NO synthase.

According to a further aspect, the present invention provides a method for the treatment of a human or animal subject suffering from a condition where there is an advantage in inhibiting NO production from L-arginine by the action of NO synthase which comprises administering to the subject an effective amount to relieve said condition of a compound of formula (I) as defined above or a pharmaceutically acceptable salt, ester or amides thereof.

The activity of a compound as an inhibitor of the enzyme NO synthase can be determined by an assay in which a macrophage cell line (J774) is induced to express NO synthase with lipopolysaccharide (LPS) and interferon gamma and NO generated is measured by its reaction with haemoglobin or as nitrite. This assay has the advantage of convenience but does not distinguish between selective and non-selective NO synthase inhibitors. Selectivity can be determined by use of an assay based on rat aortic rings in vitro. The basal tone of the tissue is used as an indication of the activity of the constitutive NO synthase whereas LPS-induced loss of tone mediated by NO is used as an indication of the activity of the inducible enzyme in the vascular smooth muscle cells. Selectivity can also be demonstrated by use of an assay based on the measurement of rat blood pressure (constitutive enzyme) and rat blood pressure in LPS treated rats (inducible enzyme). Compounds of formula (I) show activity as inhibitors of NO synthase in the J774 cell line and a number of compounds have also been demonstrated to be selective inhibitors in the rat aortic ring, in particular they have been demonstrated to be some 10 to 40 times more potent as inhibitors of the inducible NO synthase than the constitutive NO synthase.

Conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

There is also a growing body of evidence for the existence of a third NO synthase enzyme which may be involved in the degeneration of cartilage which takes place in certain conditions such as arthritis and it is also known that NO synthesis is increased in rheumatoid arthritis. Accordingly further conditions in which there is an advantage in inhibiting NO production from L-arginine include autoimmune and/or inflammatory conditions affecting the joints, for example arthritis.

As used herein, reference to "treatment" of a patient is intended to include prophylaxis.

Certain compounds of formula (I) are novel and according to a further aspect the invention provides amidino derivatives of the formula (IA)

(IA)

and salts, and pharmaceutically acceptable esters and amides thereof, in which:

$R^1$ is a $C_{1-6}$ straight or branched chain alkyl group, a $C_{2-6}$ alkenyl group, a $C_{2-6}$ alkynyl group, a $C_{3-6}$ cycloalkyl group or a $C_{3-6}$ cycloalkyl$C_{1-6}$ alkyl group;

Q is an alkylene, alkenylene or alkynylene group having 3 to 6 carbon atoms and which may optionally be substituted by one or more $C_{1-3}$ alkyl groups;

a group of formula —$(CH_2)_pX(CH_2)_q$— where p is 2 or 3, q is 1 or 2 and X is $S(O)_x$ where x is 0, 1 or 2, O or $NR^2$ where $R^2$ is H or $Cl_{1-6}$ alkyl; or a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$ alkyl, $C_{1-6}$ alkoxy, hydroxy, halo, nitro, cyano, trifluoro$C_{1-6}$ alkyl, amino, $C_{1-6}$ alkylamino or di$C_{1-6}$ alkylamino;

with the proviso that Q is neither $CH_2CH_2CH_2CH_2$ nor $CH_2CH_2CH_2$ when $R^1$ is methyl, or $CH_2CH_2CH_2$ when $R^1$ is ethyl.

According to another aspect, the present invention also provides compounds of formula (IA) as defined above and pharmaceutically acceptable salts, esters and amides thereof for use in therapy, in particular the therapy of conditions where there is an advantage in inhibiting NO production from L-arginine by the action of NO synthase.

Specific examples of the group $R^1$ include methyl, ethyl, n-propyl, isopropyl, cyclopropyl, propenyl, n-butyl, t-butyl, cyclobutyl and cyclopropylmethyl.

Specific examples of the group A as a carbocyclic or heterocyclic ring include cyclohexyl, cyclopentyl cyclobutyl, cyclopropyl, cyclohexenyl, cyclopentenyl, cyclobutenyl, phenyl, pyridyl, piperidinyl, pyrrolyl, pyrrolidinyl, furanyl, tetrahydrofuranyl, thiazolyl, imidazolyl and oxazolyl. In each case the ring may optionally be substituted by one or more suitable substituents such as the substituents mentioned above.

Particular examples of Q as an alkylene, alkenylene or alkynylene group includes groups of the formulae —$(CH_2)_n$— where n is 3 to 5;

—$(CH_2)_vCH=CH(CH_2)_w$; and

—$(CH_2)_vC\equiv C(CH_2)_w$; where in each case v is 0 to 3 and w is 0 to 3 with the proviso that the sum total of v+w is 2 to 4.

A preferred group of compounds of formula (I) are compounds in which:

$R^1$ is methyl;

Q is —$(CH_2)_n$— where n is 3 to 5, more preferably 3 or 4;

—$CH_2CH=CHCH_2$—;

—$(CH_2)_pX(CH_2)_q$— where p is 2 or 3, q is 1 or 2 and X is $S(O)_x$ where x is 0, 1 or 2, more preferably 0, O or $NR^2$ where $R^2$ is H or $C_{1-6}$ alkyl, more preferably $C_{1-3}$ alkyl; or —$(CH_2)_rA(CH_2)_s$— where r is 1 or 2, s is 1 or 2 and A is a 6 membered carbocyclic or heterocyclic ring, more preferably one of the specific rings referred to above, most preferably cyclobutyl, phenyl or pyridyl;

with the proviso that the group

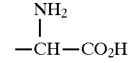

has the natural L or (S) chirality;
and pharmaceutically acceptable salts, esters and amides thereof.

A particularly preferred group of compounds of formula (I) are compounds in which:

$R^1$ is methyl;

Q represents —$(CH_2)_n$— where n is 3 or 4;

—$CH_2CH=CHCH_2$—;

—$(CH_2)_2SCH_2$—; or

—$CH_2ACH_2$— where A is cyclopropyl;

and pharmaceutically acceptable salts, esters and amides thereof.

Specific preferred compounds of formula (I) are:

(S)-$N^5$-(1-iminoethyl)ornithine;

(S)-$N^6$-(1-iminoethyl)lysine;

(±)-E-2-amino-6-(1-iminoethylamino)-hex-4-enoic acid; and (S)-S-2-(1-iminoethylamino)ethylcysteine and pharmaceutically acceptable salts, esters and amides thereof.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of formula (I) can be made by reacting the appropriate compound in the form of the free base with the appropriate acid.

Whilst it may be possible for the compounds of formula (I) to be administered as the raw chemical, it is preferable to present them as a pharmaceutical formulation. According to a further aspect, the present invention provides a pharmaceutical formulation comprising a compound of formula (I) or (IA) or a pharmaceutically acceptable salt or solvate thereof, together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.1 to 500 mg/kg per day. The dose range for adult humans is generally from 5 mg to 35 g/day and preferably 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However the dose employed will depend on a number of factors, including the age and sex of the patient, the precise disorder being treated, and its severity. Also the route of administration may vary depending on the condition and its severity.

Compounds of formula (I) can be prepared by reaction of an amino acid of formula (II)

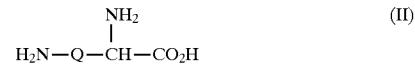

or a protected derivative thereof, with a compound of formula (III)

where L is a leaving group and $R^1$ and Q are as defined above, followed by removal of any protecting groups present.

Suitable leaving groups L include $—OR^5$ and $—SR^5$ where $R^5$ is a lower alkyl group, e.g. $C_{1-4}$alkyl, preferably methyl or ethyl.

The compound of formula (II) will generally be used in a form in which the amino acid functionality is protected by suitable protecting groups and in this connection reference can be made to T. W. Greene and P. G. M. Wuts, Protective Groups in Organic Synthesis, 2nd Edition, John Wiley and Sons Inc., 1991. The protecting groups can then be removed in conventional manner (loc. cit.) as the final stage of the process to yield the compound of formula (I). For example the amino acid functionality can be protected as the copper salt with deprotection taking place on an ion exchange column which is employed to remove inorganic ions from the reaction mixture.

The compounds of formula (III) can be used in the form of the free base or as an acid addition salt, e.g. the hydrochloride or hydroiodide salt.

The reaction is generally carried out in a suitable solvent in the presence of base, e.g. an alkali metal hydroxide such as sodium hydroxide, preferably at a pH of about 9 to 11 and generally at a temperature from 0° C. up to the reflux temperature of the solvent, preferably 0° C. to 50° C. The preferred solvent is water although the reaction may also be carried out in a polar solvent such as a lower alcohol, e.g. methanol or ethanol, or an amide, e.g. dimethylformamide, either alone or in admixture with water, and this may be advantageous in certain circumstances.

The compounds of formula (II) are in general known compounds which can be converted into appropriate protected derivatives in known manner. The imidates and thioimidates of formula (II) (L is —$OR^5$ and —$SR^5$ respectively) are also in general known compounds and the reaction of such compounds with a primary amine is discussed for example in The Chemistry of Amidines and Imidates, Vol. 2, Eds. Saul Patai and Zvi Rappaport, John Wiley and Sons Inc., 1991.

The invention is illustrated by the following Examples.

EXAMPLES

Example 1

(S)-$N^5$-(1-Iminoethyl)ornithine hydrochloride

L-Ornithine hydrochloride (10.1 g, 60 mmol) was dissolved in hot-water (10 ml) and the solution was stirred at 100° during the portionwise addition of copper carbonate (7 g) over 15 minutes. The dark blue solution was cooled to room temperature, filtered, and the residue was washed with water (20 ml).

The combined filtrate and washings were stirred at 5° during the portionwise addition of ethyl acetimidate hydrochloride (11.1 g, 90 mmol); throughout the addition the solution was maintained at a pH of 10.5 by simultaneous addition of 2N aqueous sodium hydroxide. The solution was then allowed to stand at room temperature for one hour, acidified with 2N aqueous hydrochloride to pH3 and applied to a column (150 ml) of cation exchange resin Bio-Rad AG 50W-X8 (hydrogen form). The column was washed with water until the eluate was neutral and then eluted with 0.5N aqueous ammonia. The ninhydrin positive fractions were combined and evaporated under reduced pressure at 40° C. for a short time to remove ammonia. The solution was then carefully acidified to pH4 with 2N aqueous hydrochloric acid and evaporated to dryness under reduced pressure.

The residue was crystallised by dissolving in a little water, adding a large volume of ethanol and allowing the mixture to stand at 40° for a few hours. The precipitate was filtered, washed with ethanol, and dried in a desiccator under reduced pressure to give the title compound as a colourless crystalline solid mp. 226°–228°.

Example 2

(S)-$N^6$-(1-Iminoethyl) lysine hydrochloride

Essentially by the methods of Example 1 L-lysine hydrochloride (7.3 g, 4 mmol) was converted to the copper complex which was reacted with ethyl acetimidate hydrochloride (7.5 g, 60 mmol). The title compound, isolated as described in Example 1, was obtained as a hygroscopic amorphous powder.

Example 3

(±)-E-2-Amino-6-(1-Iminoethylamino)-hex-4-enoic acid hydrochloride

The methods of Example 1 were used to convert E-4,5-dehydrolysine hydrochloride to the title compound which was obtained in an amorphous state, homogenous by t.l.c. in a mixture of acetonitrile/water/acetic acid (5:3:2), and with n.m.r. spectrum ($D_2O$) and mass spectrum consistent with the proposed structure.

Example 4

(S)-S-2-(1-Iminoethylamino)ethylcysteine hydrochloride

Using the methods of Example 1 (S)-S-2-(1-aminoethylcysteine hydrochloride (2 g, 10 mmol) was converted to the copper complex, and reacted with ethyl acetimidate hydrochloride (1.88 g, 15 mmol). The product was isolated as described in Example 1 to give the title compound as a pale yellow amorphous solid, homogeneous by t.l.c. in a mixture of acetonitrile/water/acetic acid (5:3:2), and with n.m.r. spectrum ($D_2O$) and mass spectrum consistent with the proposed structure.

The compounds of Examples 5 to 11 were prepared, essentially by the methods of Example 1, by reaction of the copper complex of the appropriate amino acid of formula (II) with the relevant ethyl alkanimidate hydrochloride.

Example 5

(S)-$N^6$-(1-Iminopropyl) lysine hydrochloride

The title compound was isolated as a hygroscopic amorphous white powder, homogeneous by t.l.c. in a mixture of acetonitrile/water/acetic acid (5:3:2).

Mass spectrum: $(M+1)^+$, 202.0.

Example 6

(S)-$N^6$-(α-Iminocyclopropylmethyl)lysine hydrochloride

The title compound was isolated as a hygroscopic amorphous white powder, homogeneous by t.l.c.

Mass spectrum: $(M+1)^+$, 214.0.

Example 7

(±)-2-Amino-7(1-iminoethylamino)-heptanoic acid hydrochloride

The title compound was obtained as amorphous material, homogeneous by t.l.c., in a mixture of acetonitrile/water/acetic acid (5:3:2).

Mass spectrum: $(M+1)^+$, 202.0.
$^1$H-NMR (200 M-Hz, $D_2O$): 1.22–1.43 (m, $2CH_2$), 1.50–1.70 (m $CH_2$), 1.75–1.90 (m, $CH_2$), 2.1 (s, $CH_3$), 3.10–3.20 (t, $CH_2$), 3.60–3.72 (t, CH).

Example 8

(±)-Z-2-Amino-6-(1-iminoethylamino)-hex-4-enoic acid hydrochloride

The title compound crystallised from a mixture of ethanol and water to give colourless crystals, mp. 223°–225°, homogeneous by t.l.c. in a mixture of methanol/0.880 ammonia (7:3).

Mass spectrum: (M+1)+,186.0. ²H-NMR (200 M-Hz, D₂O): 2.22 (s, CH₃), 2.66–2.76 (m, CH₂), 3.80–3.90 (t, CH) 3.80–4.00 (d, CH₂), 5.70–5.80 (m, 2 CH).

Example 9

(S) -N⁵-(1-Iminoprop-1-yl) ornithine hydrochloride

The title compound was obtained as a pale yellow amorphous solid, homogeneous by t.l.c. in a mixture of acetonitrile/water/acetic acid (5:3:2).

Mass spectrum: (M+1)+,188.0. ²H-NMR (200 M-Hz, D₂O): 1.05–1.08, (t, CH₃), 1.55–1.90 (m, 2CH₂), 2.30–2.45 (q, CH₂), 3.13–3.28 (t, CH₂), 3.62–3.72 (t, CH).

Example 10

(S)-N⁵-(1-Iminobut-2-yl) ornithine hydrochloride

The title compound crystallised from ethanol containing a trace of water to give a crystalline solid mp. 202°, homogeneous by t.l.c., in a mixture of acetonitrile/water/acetic acid (5:3:2). ¹H-NMR (200 M-Hz, D₂O): 1.21–1.29, (d, 2CH₃), 1.61–1.85 (m, CH₂), 1.82–2.01 (m, CH₂) 2.65–2.88, (s, CH), 3.25–3.39 (t, CH₂), 3.74–3.84 (t, CH).

Example 11

(S) -N⁵-(α-Iminocyclopropylmethyl)ornithine hydrochloride

The title compound crystallised from a mixture of ethanol and water to give a colourless crystalline solid mp. 2.75°–2.77°, homogeneous by t.l.c., in a mixture of acetonitrile/water/acetic acid (5:3:2).

Mass spectrum: (M+1)+,200. ¹H-NMR (200 M-H_z, D₂O): 1.0–1.30 (m, 2CH₂), 1.60–2.05 (m, 2CH₂, CH), 3.25–3.40 (t, CH₂), 3.70–3.85 (t, CH).

Biological Data

The activity of certain compounds of formula (I) as NO synthase inhibitors has been determined in the following assays:

Constitutive NO synthase—method of Rees et al, Br. J. Pharmacol., 101, 746–752 (1990)

Inducible NO synthase—method essentially according to Rees et al, Biochem. Biophys. Res. Comm., 173, 541–547 (1990).

The results were as follows:

| Compound of Example No. | NO Synthase Activity | | |
|---|---|---|---|
| | Constitutive EC₅₀ μM | Inducible EC₅₀ μM | EC₅₀ ratio |
| 1 | 5.1 | 0.14 | 36.4 |
| 2 | 6.9 | 0.16 | 43.1 |
| 3 | 3.1 | 0.32 | 9.7 |
| 4 | 4.3 | 0.13 | 33.4 |

We claim:
1. A compound of the formula:

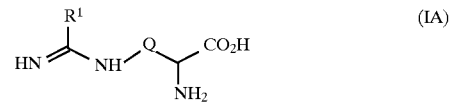

(IA)

wherein:
R¹ is methyl; Q is —CH₂CH=CHCH₂—, —(CH₂)$_p$X(CH₂)$_q$— where p is 2 or 3, q is 1 or 2 and X is S(O)$_x$ where x is 0, 1 or 2, O or NR² where R² is H or C$_{1-6}$ alkyl or —(CH₂)$_r$A(CH₂)$_s$— where r is 1 or 2, s is 1 or 2 and A is cyclobutyl, phenyl or pyridyl; with the proviso that the group

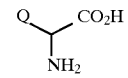

has the natural L chirality;
or a pharmaceutically acceptable salt, a pharmaceutically acceptable ester wherein —CO₂H is replaced by —CO₂R³, with R³ being selected from C$_{1-6}$ alkyl, aryl or aryl C$_{1-3}$ alkyl, or a pharmaceutically acceptable amide thereof wherein —CO₂H is selected with COR⁴ with R⁴ being an amino acid.

2. A compound as claimed in claim 1 wherein x is 0 or R² is C$_{1-3}$ alkyl.

3. A compound as of the formula:

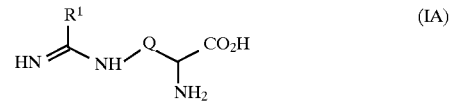

(IA)

wherein:
R¹ is methyl; Q is —CH₂CH=CHCH₂—, —(CH₂)₂SCH₂— or —CH₂ACH₂— where A is cyclopropyl; or a pharmaceutically acceptable salt, a pharmaceutically acceptable ester wherein —CO₂H is replaced by —CO₂R³, with R³ being selected from C$_{1-6}$ alkyl, aryl or aryl C$_{1-3}$ alkyl, or a pharmaceutically acceptable amide thereof wherein —CO₂H is replaced with —COR⁴ with R⁴ being an amino acid.

4. A method for the treatment of a human or animal subject suffering from a condition where therapeutic benefit is provided by selectively inhibiting NO production from L-arginine by the action of inducible NO synthase which method comprises administering to the subject an effective amount to relieve said condition of a compound of claim 1, 2 or 3.

5. A method as claimed in claim 4 wherein the condition is septic shock an autoimmune disease, an inflammatory condition or arthritis.

6. A pharmaceutical composition comprising a compound as defined in claim 1, 2 or 3 or a pharmaceutically acceptable salt thereof, together with one or more pharmaceutically acceptable carriers therefor.

* * * * *